United States Patent [19]

VandenBerg

[11] Patent Number: Plant 6,313

[45] Date of Patent: Sep. 27, 1988

[54] CHRYSANTHEMUM PLANT NAMED TARA

[75] Inventor: Cornelis P. VandenBerg, Salinas, Calif.

[73] Assignee: Yoder Brothers, Inc., Barberton, Ohio

[21] Appl. No.: 920,283

[22] Filed: Oct. 17, 1986

[51] Int. Cl.[4] ..... A01H 5/00

[52] U.S. Cl. ..... Plt./74

[58] Field of Search ..... Plt./74

*Primary Examiner*—Robert E. Bagwill

*Attorney, Agent, or Firm*—Schwartz, Jeffery, Schwaab. Mack, Blumenthal & Evans

[57] ABSTRACT

A Chrysanthemum plant named Tara particularly characterized by its flat capitulum form; anemone capitulum type; white ray floret color with a yellow anemone cushion; diameter across face of capitulum of up to 7 cm at maturity when grown as a pinched spray pot mum with a diameter of anemone cushion of up to 3 cm; uniform eight week photoperiodic flowering response to short days; medium plant height when grown as a pinched pot mum, and by its spreading and prolific branching pattern.

3 Drawing Sheets

The present invention comprises a new and distinct cultivar of Chrysanthemum, botanically known as *Chrysanthemum morifolium*, and referred to by the cultivar name Tara.

Tara, identified as 83436026, was originated from a cross made by me in a controlled breeding program in Salinas, Calif., in 1982.

The female parent of Tara was the cultivar identified as Pert, disclosed in U.S. Plant Pat. No. 4,764. The male parent of Tara was the cultivar identified as Echo, disclosed in U.S. Plant Pat. No. 4,973.

Tara was discovered and selected as one flowering plant within the progeny of the stated cross by Cornelis P. VandenBerg in May of 1983, in a controlled environment in Salinas, Calif., The first act of asexual reproduction of Tara was accomplished when vegetative cuttings were taken from the initial selection in August of 1983 in a controlled environment in Salinas, Calif., by technicians working under formulations established and supervised by Cornelis P. VandenBerg.

Horticultural examination of controlled flowerings of successive generations of plantings has shown that the unique combination of characteristics as herein disclosed for Tara are firmly fixed and are retained through successive generations of asexual reproduction.

Tara has not been observed under all possible environmental conditions. The phenotype may vary significantly with variations in environment such as temperature, light intensity, and day length.

The following observations, measurements and comparisons describe plants grown in Salinas, Calif. and Leamington, Canada, under greenhouse conditions which approximate those generally used in commercial greenhouse practice.

The following traits have been repeatedly observed and are determined to be basic characteristics of Tara, which, in combination, distinguish this Chrysanthemum as a new and distinct cultivar:

1. Flat capitulum form.
2. Anemone capitulum type.
3. White ray floret color, with a yellow anemone cushion.

4. Diameter across face of capitulum up to 7 cm at maturity, with a diameter of anemone cushion of up to 3 cm when grown as a pinched spray pot mum.
5. Uniform eight week photoperiodic flowering response to short days.
6. Medium plant height, requiring 0 to 7 long days after pinch prior to short days and 1 application of 2500 ppm B-9 SP to attain a flowered plant height of 25 to 35 cm for year-round flowerings when grown as a pinched pot mum.
7. Branching pattern is spreading and prolific.

The accompanying photographic drawings show typical inflorescence and leaf characteristics of Tara, with the colors being as nearly true as possible with illustrations of this type.

Sheet 1 is a color photograph of Tara grown as a pinched spray pot mum.

Sheet 2 is a black and white photograph of three views of the inflorescence of Tara.

Sheet 3 is a black and white photograph showing the upper and under sides of the leaves of Tara at three stages of development (mature, intermediate and immature).

Of the commercial cultivars known to the inventor, the most similar in comparison to Tara is Karma, disclosed in U.S. Plant patent application Ser. No. 765,517. Reference is made to attached Chart A, which compares certain characteristics of Tara to the same characteristics of Karma.

Traits similar to both cultivars are capitulum form, ray floret color, diameter across face of capitulum, plant height and flowering response. Tara has an anemone capitulum type, as opposed to Karma which has a daisy capitulum type. Also, Tara has a more spreading habit than Karma.

In the following description, color references are made to The Royal Horticultural Society Colour Chart. The clear white ray floret color of Tara is not represented in The Royal Horticultural Society Colour Chart. The color valueswere determined from plant material grown as a pinched spray pot mum in Salinas, Calif. on Mar. 14, 1986.

Classification:

*Botanical.*—*Chrysanthemum morifolium,* Ramat., cv. Tara.

*Commercial.*—Anemone spray pot mum.

INFLORESCENCE

A. Capitulum:

*Form.*—Flat.

*Type.*—Anemone.

*Diameter across face.*—Up to 7 cm at maturity.

*Diameter of anemone cushion.*—Up to 3 cm.

B. Corolla of ray florets:

*Color (general tonality from a distance of three meters).*—White.

*Color (upper surface).*—White.

*Color (under surface).*—White.

*Shape.*—Oblong.

C. Corolla of disc florets:

*Color (mature).*—5C.

*Color (immature).*—6B.

D. Reproductive organs:

*Androecium.*—Present in disc florets only; scant pollen.

*Gynoecium.*—Present in both ray and disc florets.

PLANT

A. General appearance:

*Height.*—Medium; 25 to 35 cm as a pinched spray pot mum with 0 to 7 long days after pinch prior to short days and 1 application of 2500 ppm B-9 SP.

*Branching pattern.*—Spreading and prolific.

B. Foliage:

*Color (upper surface).*—147A.

*Color (under surface).*—147B.

*Shape.*—Lobed and serrated.

CHART A

COMPARISON OF TARA AND KARMA

| CULTIVAR | RAY FLORET COLOR | CAPITULUM FORM & TYPE | BRANCHING PATTERN |
|---|---|---|---|
| TARA | WHITE | ANEMONE | SPREADING |
| KARMA | WHITE | DAISY | SEMI SPREADING |

| CULTIVAR | DIAMETER ACROSS FACE OF CAPITULUM | PLANT HEIGHT | FLOWERING RESPONSE PERIOD |
|---|---|---|---|
| TARA | up to 7 cm | MEDIUM | 8 weeks |
| KARMA | up to 7 cm | MEDIUM | 8 weeks |

COMPARISONS MADE OF PLANTS GROWN AS PINCHED POT MUM IN SALINAS, CALIFORNIA

I claim:

1. A new and distinct Chrysanthemum plant named Tara, as described and illustrated, and particularly characterized as to uniqueness by the combined characteristics of flat capitulum form; anemone capitulum type; white ray floret color with a yellow anemone cushion; diameter across face of capitulum of up to 7 cm at maturity when grown as a pinched spray pot mum, with diameter of anemone cushion of up to 3 cm; uniform eight week photoperiodic flowering response to short days; medium plant height when grown as a pinched pot mum, and by its spreading and prolific branching pattern.

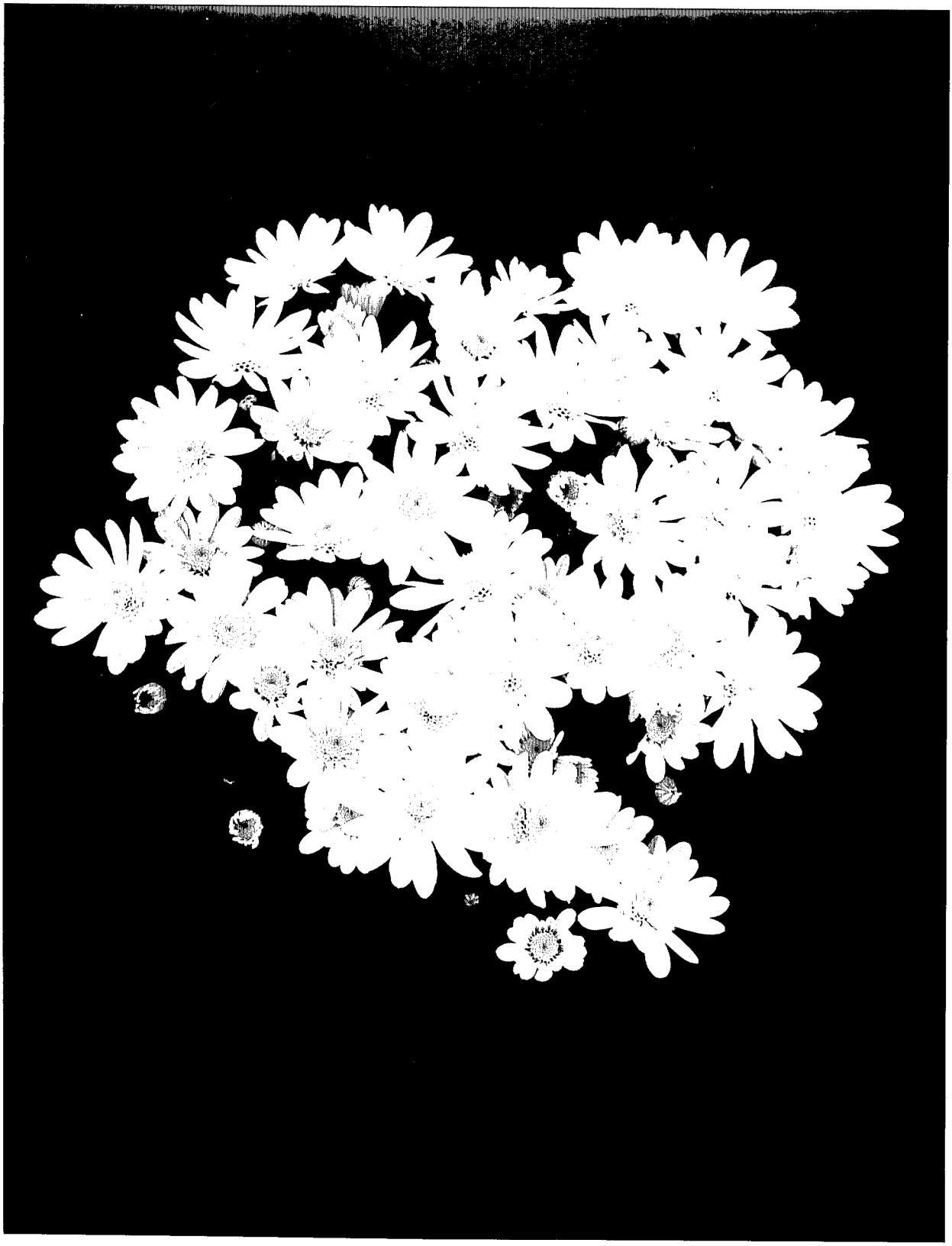

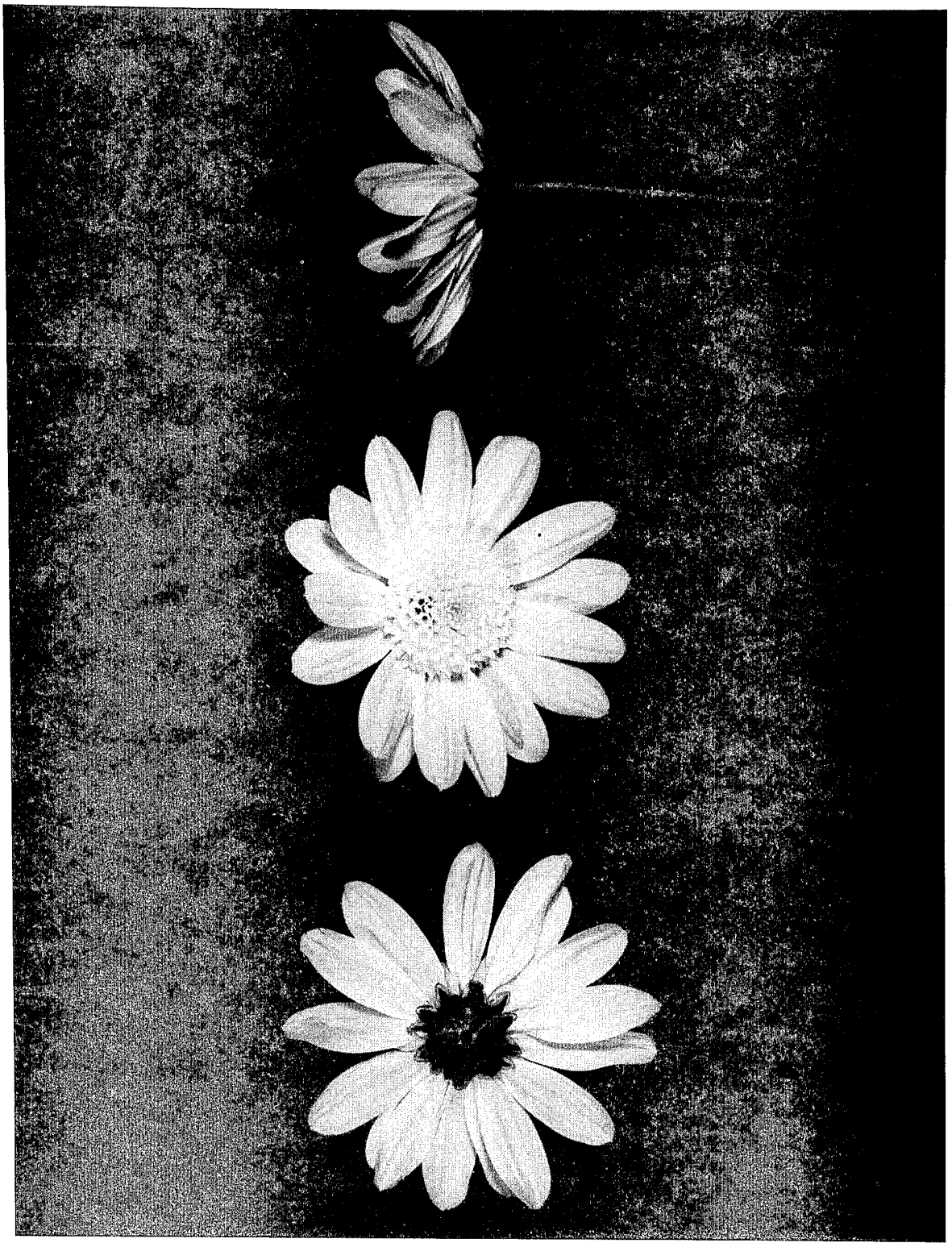

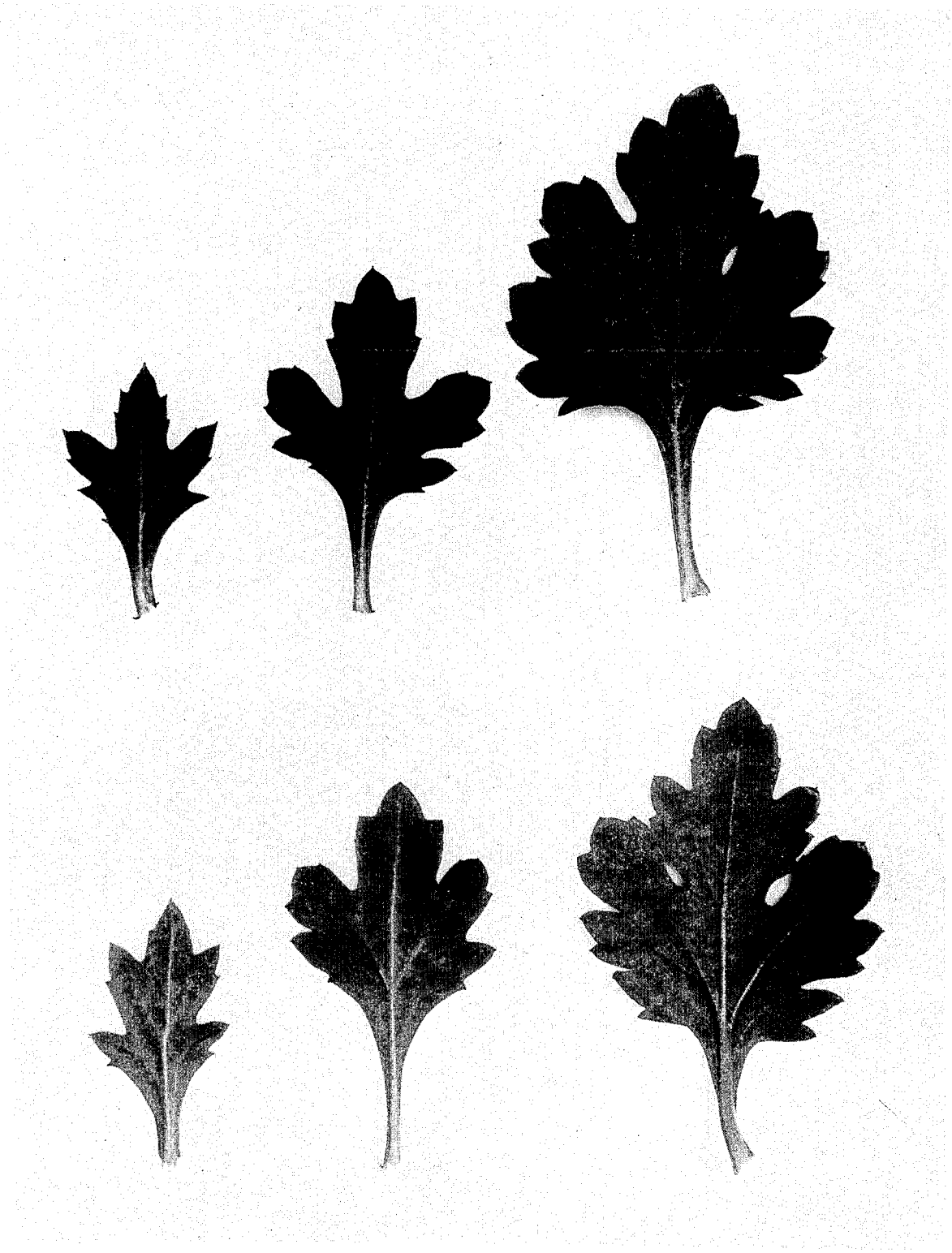

* * * * *